US005789531A

United States Patent [19]
Sumner-Smith et al.

[11] Patent Number: 5,789,531
[45] Date of Patent: *Aug. 4, 1998

[54] PEPTIDE-BASED INHIBITORS OF HIV REPLICATION

[75] Inventors: Martin Sumner-Smith, Bolton; Richard W. Barnett, Mississauga; Lorne S. Reid, Toronto; Nahum Sonenberg, St. Luc, all of Canada

[73] Assignee: Allex Biopharmaceuticals, Inc., Mississauga, Canada

[*] Notice: The term of this patent shall not extend beyond the expiration date of Pat. No. 5,646,120.

[21] Appl. No.: 475,583

[22] Filed: Jun. 7, 1995

Related U.S. Application Data

[63] Continuation of Ser. No. 357,056, Dec. 14, 1994, Pat. No. 5,646,120, which is a continuation of Ser. No. 779,735, Oct. 23, 1991, abandoned, which is a continuation-in-part of Ser. No. 602,953, Oct. 24, 1990, abandoned.

[51] Int. Cl.$^6$ ............................................. A61K 38/08
[52] U.S. Cl. ..................... 530/328; 530/327; 530/329; 514/15; 514/16; 514/17
[58] Field of Search ........................... 514/14–16, 17; 530/327–329

[56] References Cited

U.S. PATENT DOCUMENTS

| | | | |
|---|---|---|---|
| 4,042,330 | 8/1977 | Deshmukh | 436/13 |
| 4,252,784 | 2/1981 | Levine | 424/9.81 |
| 4,447,356 | 3/1984 | Olivera | 260/112.5 |
| 4,713,366 | 12/1987 | Stevens | 514/13 |
| 5,093,317 | 3/1992 | Lewis | 514/12 |
| 5,110,802 | 5/1992 | Cantin et al. | 514/44 |
| 5,135,736 | 8/1992 | Anderson et al. | 424/1.49 |
| 5,166,320 | 11/1992 | Wu et al. | 530/395 |
| 5,171,838 | 12/1992 | Chiba | 530/326 |

FOREIGN PATENT DOCUMENTS

| | | |
|---|---|---|
| 8912461 | 12/1989 | WIPO. |
| WO 89/12461 | 12/1989 | WIPO. |

OTHER PUBLICATIONS

Choppin et al. "Analysis of Physical Interactions between Peptides and HLA Molecules and Application to the Detection . . . ", *J. Exp. Med.*, 172:889–899, 1990.
Arnold, Jr., "Polylysin–Drug Conjugates," Methods in Enzymology, vol. 112, pp. 270–285 (1985).
Coy, Biochem Biophys Res Comm, 73:632, 1976.
Burger, J Biol Chem 193:13, 1951.
Docherty, Antimicrob Agents Chemother, 31:1562, 1987.
ASM News, vol. 56 No. 7 (Jul. 1990) at 368.
Spatola, "Peptide and Modifications . . . " Chemistry and Biochemistry of Aminoacids, Peptides and Proteins (Weinstein 1983) 267–357.
Ratner et al. (1985) *Nature* 313:277, "Complete nucleotide sequence of the AIDS virus, HTLV–III".
Kuppuswamy et al. (1989) *Nucleic Acids Research* 17(9): 3551, "Multiple functional domains of Tat, the trans–activator of HIV–1, defined by mutational analysis".
Hauber et al. (1989) *J. Virol.* 63(3): 1181, "Mutational analysis of the conserved basic domain of human immunodeficiencey virus tat protein".
Green et al. (1989) *Cell* 58:215, "Mutational analysis of HIV–1 tat minimal domain peptides: identification of trans–dominant mutants that suppress HIV–LTR–Driven gene expression".
Weeks et al. (1990) *Science* 249:1281, "Fragments of the HIV–I tat protein specifically bind TAR RNA".
Ruben et al. (1989) *J. Virol.* 63(1):1, "Structural and functional characterization of human immunodeficiency virus tat protein".
Roy et al. (1990) *Genes and Development* 4:1365, "A bulge structure in HIV–I TAR RNA is required for tat binding and tat–mediated trans–activation".
Green et al. (1988) *Cell* 55:1179, "Autonomous functional domains of chemically synthesized human immunodeficiency virus tat trans–activator protein".
Frankel et al. (1989) *Proc. Nat'l. Acad. Science* 86:7397, "Activity of synthetic peptides from the tat protein of human immunodeficiency virus type 1".
Stryer, (1981) *Biochemistry* 2:123–127, "Electrostatic, hydrogen, and Van Der Waals bonds in enzyme–substrate complexes".
Coy, BBRC 73, 632, 1976.
Weeks, Science 249, 1281, 1990.

*Primary Examiner*—Cecilia J. Tsang
*Assistant Examiner*—David Lukton
*Attorney, Agent, or Firm*—Foley & Lardner

[57] ABSTRACT

Described herein are oligopeptides useful to inhibit replication in virally infected individuals. In a preferred embodiment of the invention, the oligopeptide is a D-arginine nonamer having N- and C-terminal protecting groups, which, at a 3 uM concentration, exhibits greater than 95% inhibition of HIV replication, in a standard assay.

31 Claims, 1 Drawing Sheet

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
( A ) LENGTH: 9 amino acids
( B ) TYPE: amino acid
( D ) TOPOLOGY: linear (  i  i  ) MOLECULE TYPE: peptide ( x i ) SEQUENCE DESCRIPTION: SEQ ID NO:1:

Arg  Lys  Lys  Arg  Arg  Gln  Arg  Arg  Arg
1                       5

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( D ) TOPOLOGY: linear     ( i i ) MOLECULE TYPE: peptide     ( i x ) FEATURE:
        ( A ) NAME/KEY: Modified-site
        ( B ) LOCATION: 6
        ( D ) OTHER INFORMATION: /note= "Xaa represents a basic
            amino acid and corresponds to Y1 of the
            specification"

( x i ) SEQUENCE DESCRIPTION: SEQ ID NO:2:

Arg  Lys  Lys  Arg  Arg  Xaa  Arg  Arg  Arg
1                       5

( 2 ) INFORMATION FOR SEQ ID NO:3:

( i ) SEQUENCE CHARACTERISTICS:
        ( A ) LENGTH: 9 amino acids
        ( B ) TYPE: amino acid
        ( D ) TOPOLOGY: linear     ( i i ) MOLECULE TYPE: peptide     ( i x ) FEATURE:
        ( A ) NAME/KEY: Modified-site
        ( B ) LOCATION: 2
        ( D ) OTHER INFORMATION: /note= "Xaa represents a basic
            amino acid and corresponds to Y2 of the
            specification"

( i x ) FEATURE:
        ( A ) NAME/KEY: Modified-site
        ( B ) LOCATION: 3
        ( D ) OTHER INFORMATION: /note= "Xaa represents a basic
            amino acid and corresponds to Y3 of the
            specification"

( i x ) FEATURE:
        ( A ) NAME/KEY: Modified-site
        ( B ) LOCATION: 6
        ( D ) OTHER INFORMATION: /note= "Xaa represents a basic
            amino acid and corresponds to Y4 of the
            specification"

( x i ) SEQUENCE DESCRIPTION: SEQ ID NO:3:

Arg  Xaa  Xaa  Arg  Arg  Xaa  Arg  Arg  Arg
1                       5

( 2 ) INFORMATION FOR SEQ ID NO:4:

( i ) SEQUENCE CHARACTERISTICS:
        ( A ) LENGTH: 12 amino acids
        ( B ) TYPE: amino acid
        ( D ) TOPOLOGY: linear     ( i i ) MOLECULE TYPE: peptide     ( i x ) FEATURE:
        ( A ) NAME/KEY: Modified-site
        ( B ) LOCATION: 8
        ( D ) OTHER INFORMATION: /note= "Xaa represents Gly, Cys, Ser, His, Lys, Asn, or homoGln"

( x i ) SEQUENCE DESCRIPTION: SEQ ID NO:4:

Tyr Gly Arg Lys Lys Arg Arg Xaa Arg Arg Pro
1               5                    10

( 2 ) INFORMATION FOR SEQ ID NO:5:

( i ) SEQUENCE CHARACTERISTICS:
      ( A ) LENGTH: 9 amino acids
      ( B ) TYPE: amino acid
      ( D ) TOPOLOGY: linear    ( i i ) MOLECULE TYPE: peptide    ( x i ) SEQUENCE DESCRIPTION: SEQ ID NO:5:

Arg Gln Arg Arg Arg Arg Arg Arg Arg
1               5

( 2 ) INFORMATION FOR SEQ ID NO:6:

( i ) SEQUENCE CHARACTERISTICS:
      ( A ) LENGTH: 9 amino acids
      ( B ) TYPE: amino acid
      ( D ) TOPOLOGY: linear    ( i i ) MOLECULE TYPE: peptide    ( x i ) SEQUENCE DESCRIPTION: SEQ ID NO:6:

Arg Arg Gln Arg Arg Arg Arg Arg Arg
1               5

( 2 ) INFORMATION FOR SEQ ID NO:7:

( i ) SEQUENCE CHARACTERISTICS:
      ( A ) LENGTH: 9 amino acids
      ( B ) TYPE: amino acid
      ( D ) TOPOLOGY: linear    ( i i ) MOLECULE TYPE: peptide    ( x i ) SEQUENCE DESCRIPTION: SEQ ID NO:7:

Arg Arg Arg Gln Arg Arg Arg Arg Arg
1               5

( 2 ) INFORMATION FOR SEQ ID NO:8:

( i ) SEQUENCE CHARACTERISTICS:
      ( A ) LENGTH: 9 amino acids
      ( B ) TYPE: amino acid
      ( D ) TOPOLOGY: linear    ( i i ) MOLECULE TYPE: peptide    ( x i ) SEQUENCE DESCRIPTION: SEQ ID NO:8:

Arg Arg Arg Arg Gln Arg Arg Arg Arg
1               5

( 2 ) INFORMATION FOR SEQ ID NO:9:

( i ) SEQUENCE CHARACTERISTICS:
      ( A ) LENGTH: 9 amino acids
      ( B ) TYPE: amino acid
      ( D ) TOPOLOGY: linear    ( i i ) MOLECULE TYPE: peptide    ( x i ) SEQUENCE DESCRIPTION: SEQ ID NO:9:

Arg Arg Arg Arg Arg Gln Arg Arg Arg (2) INFORMATION FOR SEQ ID NO:10:

(i) SEQUENCE CHARACTERISTICS:
        (A) LENGTH: 9 amino acids
        (B) TYPE: amino acid
        (D) TOPOLOGY: linear     (ii) MOLECULE TYPE: peptide     (xi) SEQUENCE DESCRIPTION: SEQ ID NO:10:

Arg Arg Arg Arg Arg Arg Gln Arg Arg
1             5

(2) INFORMATION FOR SEQ ID NO:11:

(i) SEQUENCE CHARACTERISTICS:
        (A) LENGTH: 9 amino acids
        (B) TYPE: amino acid
        (D) TOPOLOGY: linear     (ii) MOLECULE TYPE: peptide     (xi) SEQUENCE DESCRIPTION: SEQ ID NO:11:

Arg Arg Arg Arg Arg Arg Arg Gln Arg
1             5

(2) INFORMATION FOR SEQ ID NO:12:

(i) SEQUENCE CHARACTERISTICS:
        (A) LENGTH: 12 amino acids
        (B) TYPE: amino acid
        (D) TOPOLOGY: linear     (ii) MOLECULE TYPE: peptide     (xi) SEQUENCE DESCRIPTION: SEQ ID NO:12:

Arg Arg Arg Arg Arg Arg Arg Arg Arg Arg Arg Arg
1             5                    10

(2) INFORMATION FOR SEQ ID NO:13:

(i) SEQUENCE CHARACTERISTICS:
        (A) LENGTH: 27 base pairs
        (B) TYPE: nucleic acid
        (C) STRANDEDNESS: single
        (D) TOPOLOGY: linear     (ii) MOLECULE TYPE: Other nucleic acid;
        (A) DESCRIPTION: Synthetic RNA     (xi) SEQUENCE DESCRIPTION: SEQ ID NO:13:

GGAGAUCUGA GCCUGGGAGC UCUCUCC                          27

(2) INFORMATION FOR SEQ ID NO:14:

(i) SEQUENCE CHARACTERISTICS:
        (A) LENGTH: 27 base pairs
        (B) TYPE: nucleic acid
        (C) STRANDEDNESS: single
        (D) TOPOLOGY: linear

(ii) MOLECULE TYPE: Other nucleic acid;
        (A) DESCRIPTION: Synthetic RNA     (xi) SEQUENCE DESCRIPTION: SEQ ID NO:14:

GGAGAACUGA GCCUGGGAGC UCUCUCC                          27

PEPTIDE-BASED INHIBITORS OF HIV REPLICATION

This application is a continuation of application Ser. No. 08/357,056, filed Dec. 14, 1994 now U.S. Pat. No. 5,646,120; which is a continuation of application Ser. No. 07/779,735, filed Oct. 23, 1991, now abandoned, and which is a continuation-in-part application of Ser. No. 07/602,953, filed Oct. 24, 1990, now abandoned.

After integrating into its human cell host, the human immunodeficiency virus, HIV, undergoes highly controlled stages of replication. Infection of an individual is followed initially by a phase, known as the latency period, in which viral replication is either non-existent or occurs at only a very low, basal level. In a later phase however, which marks progression of the acquired immune deficiency syndrome or AIDS, the viral replication rate is remarkably accelerated, and leads ultimately to cell death and the continued spread of infection. Studies have shown that one of the principle mediators of accelerated viral replication is an HIV-produced protein know as tat.

While select strains of HIV produce different forms of tat, a 72 amino acid N-terminal sequence is common to all forms. The principle form of tat, herein designated tat (1–86), consists of 86 amino acids arranged in the sequence reported by Ratner et al., 1985, Nature 313:277, incorporated herein by reference. Structure/function analysis of the various tat forms has revealed at least three domains in the protein, including a proline-rich region spanning residues 1–18, a cysteine-rich region spanning residues 22–37, and a basic region of nine amino acid spanning residues 49–57.

Following accumulation in its cellular environment, tat elicits a dramatic increase in the rate at which gene products essential to HIV replication are expressed, a process which is referred as a "transactivation". Recent studies demonstrate that tat's ability to amplify gene product formation is mediated through its binding interaction with an RNA hairpin structure, known as the "transactivator responsive element" or TAR element, borne at the 5' end of all HIV gene transcripts (see for example Weeks et all, infra). It has accordingly been suggested that agents capable of interfering with the interaction between tat protein and the RNA TAR element could inhibit viral replication, and thus be useful therapeutically to treat virally infected individuals. In this area of research, some effort is aimed at identifying transactivation-deficient analogues of tat that antagonize tat action by competing with it for binding to the TAR element.

Variants of tat (1–86) have been generated by the expression in genetically engineered microbial hosts of an appropriately mutagenized clone of the HIV tat gene (see example Kuppuswamy et al, Nucl. Acids Res., 1989, 17(9):3551). These variants have been useful in identifying essential structural features and in mapping functional domains of tat. Kuppuswamy et al found, for example, that tat analogues bearing substitutions in the cysteine-rich domain of tat (residues 22–37) were almost totally defective in transactivation, and postulated that the cysteine residues were essential for tat activity. Also defective in transactivation were tat analogues lacking the basic domain (residues 49–57). The authors suggest that the basic domain is important also cell uptake of tat, and for efficient transport of tat to the nucleus.

Mutational analysis of the basic domain of tat has been reported also by Hauber at al in J. Virol., 1989, 63(3):1181, who showed that the transactivation function of tat in markedly reduced when positively charged amino acids in the basic domain of tat (1–86) are replaced by neutral amino acid residues.

Green at al have also studied the transactivation function of various tat fragments (see Cell, July 1989, 58:215). While an oligopeptide representing tat residues 37–72 was found to mediate transactivation, variants thereof bearing substitutions at residues 41, 46 or 47 displayed negligible transactivation, and are described by the authors as potential antagonists of tat action (see also Green at al, in WO89/12461 published 28 Dec. 1989). Weak tat antagonist activity was also detected in an oligopeptide representing the basic domain of tat (SEQ ID NO:1) i.e. $^{49}$Arg—Lys—Lys—Arg—Arg—Gln—Arg—Arg—Arg$^{57}$.

Weeks et al, in a highly refined study, have confirmed that tat does indeed bind to the HIV TAR element, and have pointed more specifically to a binding interface between the tat basic domain and a three nucleotide bulge extending from the stem of the TAR hairpin (see Science, 1990, 249:1281).

It is a general object of the present to provide a compound useful to inhibit replication of the immunodeficiency virus, HIV.

It is a more specific object of the present invention to provide a compound capable of inhibiting tat-mediated transactivation of HIV gene expression.

It is another object of the present invention to provide a pharmaceutical composition useful to inhibit replication of HIV.

SUMMARY OF THE INVENTION

It has now been found that the tat antagonist properties of the tat basic domain can be improved through structural modification thereof. It has more specifically been found that alterations in the amino acid sequence constituting the tat basic domain can confer enhanced TAR-binding affinity, thus providing compounds better able to compete with endogenous tat for binding to TAR. It has further been found that the TAR-binding affinity of the tat basic domain is not substantially compromised when the L-amino acids which occur naturally in its sequence are replaced with the less protease-sensitive D-amino acids. Advantageously, none of the modifications herein described alter the highly basic amino acid composition responsible for both cellular uptake and nuclear localization of tat. Moreover, the tat basic domain analogues of the present invention bind to the HIV TAR element with a selectivity similar to that exhibited by tat.

More particularly, and according to one aspect of the invention, there is provided a transactivation-deficient, HIV TAR-binding compound of the formula:

wherein

R1 is 2 or an N-terminal protecting group;

R2 is OH or a carboxyl terminal protecting group;

X represents a TAR-binding, transactivation-deficient oligopeptide analogue of the tat basic domain, consisting of from 7 to 12 amide-linked α-amino acid residues;

m is 0 or 1;

n is 0 or 1; and

A and B independently represent one or more amide-linked, α-amino acid residues which collectively are selected to retain the transactivation-deficient nature of the compound.

According to one embodiment of the invention, X in the above formula represents an oligopeptide having a TAR binding affinity that is enhanced relative to HIV tat. According to another embodiment of the present invention, X in the above formula represents an oligopeptide comprising at least one D-amino acid, and more desirably consists essentially of D-amino acids. A preferred compound of the present invention consists of nine D-arginine residues having blocking groups at both the N- and C-termini.

According to another aspect of the present invention, there is provided a pharmaceutical composition comprising a transactivation-deficient, TAR-binding compound of the invention, and a pharmaceutically acceptable carrier.

According to another aspect of the present invention, there is provided a method for treating a patient infected with HIV, which comprises administering to the patient an effective amount of a compound of the present invention.

The terms "amino acid" and "α-amino acid residue" are used interchangably herein with reference to naturally occurring and synthetic amino acids in either D- or L- form. Unless otherwise stated, the amino acid is the naturally occurring L-amino acid. Included, unless otherwise stated, are are the amino acids glycine; those amino acids having an aliphatic α-carbon side chain such as alanine, valine, norvaline, leucine, norleucine, isoleucine and proline; those having aromatic α-carbon side-chains such as phenylalanine, tyrosine and tryptophan; those having acidic α-carbon side chains such as aspartic acid and glutamic acid; those having side chains which incorporate a hydroxyl group such as serine, homoserine, hydroxynorvaline, hydroxyproline and threonine; those having sulfur-containing α-carbon side chains such as cysteine and methionine; those having side chains incorporating an amide group such an glutamine and asparagine; and those having basic α-carbon side chains such as lysine, arginine, histidine, and ornithine (also herein referred to as "basic amino acids").

The term "N-protecting group" refers to a radical attached to the nitrogen atom which serves to protect the amino terminus of the oligopeptide from undesired biochemical attack.

The term "carboxyl protecting group" refers to a radical attached to the C-terminus of the oligopeptide either via an oxygen or via the carbon of the terminal carboxyl group, which serves to protect the carboxyl terminus of the oligopeptide from undesired biochemical attack.

BRIEF REFERENCE TO THE DRAWINGS

DETAILED DESCRIPTION OF THE INVENTION AND ITS PREFERRED EMBODIMENTS

The compounds of the invention are transactivation-deficient, TAR-binding oligopeptides, which function as antagonists of tat action.

The terms "oligopeptide" and "polypeptide" are used interchangably herein with reference to a compound having from about 6 to about 100 or more amide-linked α-amino acid residues.

The term "transactivation" refers to the tat-mediated enhancement of HIV gene expression, which results in elevated viral mRNA level and activity, probably as a result of tat-mediated effects on transcription from the viral long terminal repeat (LTR—which includes the sole viral promoter) and perhaps on tat-mediated effects on translation. The transactivation effect of a given compound can be determined directly by incubating the compound with HIV-infected cells and then measuring the increase in viral plaque formation, or the increase in production of one or more viral proteins, such as p24. Assays more convenient for measuring transactivation have been developed and, because they do not require use of intact virus, are now more commonly used. In these assays, a candidate compound is incubated with mammalian cells harbouring recombinant DNA cassettes in which DNA coding for a conveniently detectable marker protein is placed under the expression control of the HIV LTR. Formation of marker protein following uptake of the candidate compound is thus a direct measure of its ability to mediate transactivation. An example of one such convenient transactivation assay, which employs a bacterial chloramphenicol transferase (CAT) as the marker protein, is described by Ruben et al in J. Virol., 1989, 63(1):1.

The term "transactivation deficient" used herein to characterize compounds of the invention thus refers to oligopeptides and polypeptides which following cell uptake are incapable of mediating a statistically significant increase in LTR-mediated gene expression, as measured by any one of the conventionally used means for detecting transactivation.

The term "TAR-binding", used herein to characterize compounds of the invention, refers to compounds which exhibit the ability to bind the HIV TAR element, as determined by an RNA mobility shift electrophoresis assay (see for example Roy et al, infra). This assay generally involves the incubation of a selected oligopeptide with gel-purified, radio-labelled TAR RNA, or tat-binding fragment of TAR RNA, that has been produced either by direct synthesis or through transcription of a corresponding DNA template. Samples are loaded onto non-denaturing polyacrylamide gel and subjected to electrophoresis, and then migration of labelled RNA through the gel is visualized on gel-exposed, X-ray film. Oligopeptides which bind TAR are identified in this assay by their characteristic, retarded migration on the gel, relative to TAR RNA to which no oligopeptide has bound. In this mobility shift assay, oligopeptides having an "enhanced" affinity for binding TAR RNA will resolve on the gel as bands which, in addition to displaying the retarded migration pattern characteristic of TAR-binding oligopeptides, will also appear with greater intensity and/or size than a band containing TAR RNA bound to tat (1–86).

The term "basic domain" refers to the basic domain of the HIV tat protein, which is an oliogopeptide consisting of nine L-amino acids arranged in the sequence (SEQ ID NO:1) Arg—Lys—Lys—Arg—Arg—Gln—Arg—Arg—Arg. Oligopeptides which differ from the basic domain in terms of amino acid sequence, either by way of addition, deletion or replacement of one or more amino acids including replacement of an L-amino by a corresponding D-amino acid, are referred to herein as "analogues" of the tat basic domain.

In one of its aspects, the present invention provides Tar-binding, transactivation deficient compounds which conform to the general formula (I)

R1—(A)m—[X]—(B)n—R2        (I)

wherein:

X represents a Tar-binding, transactivation deficient oligopeptide analogue of the basic domain of the HIV tat protein i.e. an analogue of the amino acid sequence (SEQ ID NO:1) Arg—Lys—Lys—Arg—Arg—Gln—Arg—Arg—Arg, which consists of from 7 to 12 amide-linked α-amino acids;

A represents one or more amide-linked, α-amino acids coupled to the N-terminus of X;

B represents one or more amide-linked, α-amino acids coupled to the C-terminus of X, with the proviso that both A and B are selected such that the compound of formula I exhibits both Tar-binding affinity and transactivation-deficiency;

m and n are, independently, either 0 or 1;
R1 represents H or an N-protecting group (Np); and R2 represents OH or a carboxyl-protecting group (Cp).

Preferred compounds of the present invention are those of formula (Ia),

R1—|X|—R2 (Ia)

in which R1, R2 and X are as specified above.

Particularly preferred are compounds of formula (Ib),

Np—|X|—Cp (Ib)

in which X is as specified above. Np represents an N-terminal protecting group, and Cp represents a carboxyl terminal protecting group.

In each of the above formulae I, Ia and Ib, X represents an oligopeptide consisting of from 7 to 12 amide-linked amino acid residues, preferably 8 to 10 amino acid residues, arranged in a sequence that confers TAR-binding affinity. According to a preferred aspect of the present invention, X comprises at least one amino acid in the D-isomer form. The oligopeptide X may, for example, comprise alternating L- and D-amino acids. Most preferably the oliogopeptide consists essentially of D-amino acids. With respect to amino acid composition, X in each of the above formulae I, Ia and Ib is an oligopeptide analogue of the HIV tat basic domain desirably having a net positive charge of at least n−1where n represents the number of amino acids constituting the oligopeptide X. With respect to composition and sequence, X is selected desirably from among the group consisting of;

i) an oligopeptide having the sequence (SEQ ID NO:1) Arg—Lys—Lys—Arg—Arg—Gln—Arg—Arg—Arg, wherein at least one amino acid is a D-amino acid;

ii) an oligopeptide consisting of from 6 to 11 basic amino acids and one amino acid other than a basic amino acid, wherein each basic amino acid is independently selected from among the group consisting of arginine, lysine, histidine and ornithine, and said one amino acid is selected from among the group consisting of glutamine, serine, histidine, lysine, asparagine and homoglutamine. Especially suitable oligopeptides are those in which each basic amino acid is independently selected from arginine and lysine, and the non-basic amino acid is glutamine; and iii) an oligopeptide consisting essentially of from 7 to 12 basic amino acids, wherein each basic amino acid residue is independently selected from among the group consisting of lysine and arginine.

According to specific embodiments of the present invention, X represents an oligopeptide selected from among the group consisting of:

iv) an oligopeptide comprising amino acids arranged in the sequence (SEQ ID NO:2) Arg—Lys—Lys—Arg—Arg—Y1—Arg—Arg—Arg, wherein Y1 is a basic amino acid;

v) an oligopeptide comprising amino acids arranged in the sequence (SEQ ID NO:3) Arg—Y2—Y3—Arg—Arg—Y4—Arg—Arg—Arg wherein each of Y2, Y3 and Y4 is a basic amino acid, and at least one of Y2, Y3 and Y4 is arginine;

vi) an oligopeptide comprising from 6 to 11 arginines and one glutamine; and vi) an oligopeptide homopolymer consisting of from 7 to 12 arginines.

According to preferred embodiments of the present invention, X in the above formula I, Ia and Ib represents an oligopeptide, preferably consisting essentially of D-amino acids, having an amino acid sequence selected from:

Arg—Lys—Lys—Arg—Arg—Lys—Arg—Arg—Arg (SEQ ID NO:2 wherein Xaa is Lys);

Arg—Lys—Lys—Arg—Arg—Ser—Arg—Arg—Arg (SEQ ID NO:2 wherein Xaa is Ser);

Arg—Lys—Lys—Arg—Arg—Arg—Arg—Arg—Arg (SEQ ID NO:2 wherein Xaa is His);

Arg—Lys—Lys—Arg—Arg—His—Arg—Arg—Arg (SEQ ID NO:2 wherein Xaa is Asn);

Arg—Lys—Lys—Arg—Arg—homoGln—Arg—Arg—Arg (SEQ ID NO:2 wherein Xaa is homoGln);

Arg—Lys—Lys—Arg—Arg—Arg—Arg—Arg—Arg (SEQ ID NO:3 wherein Xaa at position 2 is Lys, Xaa at position 3 is Lys, and Xaa at position 6 is Arg.);

Arg—Lys—Arg—Arg—Arg—Arg—Arg—Arg—Arg (SEQ ID NO:3 wherein Xaa at position 2 is Lys, Xaa at position 3 is Arg, and Xaa at position 6 is Arg.);

Arg—Arg—Lys—Arg—Arg—Arg—Arg—Arg—Arg (SEQ ID NO:3 wherein Xaa at position 2 is Arg, Xaa at position 3 is Lys, and Xaa at position 6 is Arg.);

Arg—Arg—Lys—Arg—Arg—Lys—Arg—Arg—Arg (SEQ ID NO:3 wherein Xaa at position 2 is Arg, Xaa at position 3 is Lys, and Xaa at position 6 is Lys.);

Arg—Arg—Arg—Arg—Arg—Lys—Arg—Arg—Arg (SEQ ID NO:3 wherein Xaa at position 2 is Arg, Xaa at position 3 is Arg, and Xaa at position 6 is Lys.);

Arg—Gln—Arg—Arg—Arg—Arg—Arg—Arg—Arg (SEQ ID NO:5);

Arg—Arg—Gln—Arg—Arg—Arg—Arg—Arg—Arg (SEQ ID NO:6);

Arg—Arg—Arg—Gln—Arg—Arg—Arg—Arg—Arg (SEQ ID NO:7);

Arg—Arg—Arg—Arg—Gln—Arg—Arg—Arg—Arg (SEQ ID NO:8);

Arg—Arg—Arg—Arg—Arg—Gln—Arg—Arg—Arg (SEQ ID NO:9);

Arg—Arg—Arg—Arg—Arg—Arg—Gln—Arg—Arg (SEQ ID NO:10);

Arg—Arg—Arg—Arg—Arg—Arg—Arg—Gln—Arg (SEQ ID NO:11);

Arg—Arg—Arg—Gln—Arg—Arg—Arg (amino acid residues 1–7 of SEQ ID NO:7);

Arg—Arg—Arg—Arg—Arg—Arg—Arg (amino acid residues 1–7 of SEQ ID NO:12);

Arg—Arg—Arg—Arg—Arg—Arg—Arg—Arg (amino acid residues 1–8 of SEQ ID NO:12);

Arg—Arg—Arg—Arg—Arg—Arg—Arg—Arg—Arg (amino acid residues 1–9 of SEQ ID NO:12);

Arg—Arg—Arg—Arg—Arg—Arg—Arg—Arg—Arg—Arg (amino acid residues 1–10of SEQ ID NO:12);

Arg—Arg—Arg—Arg—Arg—Arg—Arg—Arg—Arg—Arg—Arg (Amino acid residues 1–11 of SEQ ID NO:12); and Arg—Arg—Arg—Arg—Arg—Arg—Arg—Arg—Arg—Arg—Arg—Arg (SEQ ID NO:12).

Particularly preferred compounds of the present invention are those of formula I, Ia and Ib in which X represents either homopolymeric D-arginine, having 8, 9 or 10 amide-linked D-arginine residues, or an oligopeptide comprising one at least one D-Gln residue and 7, 8 or 9 D-Arg residues. The presently most preferred compounds are those wherein X in the above formulae I, Ia and Ib represents an oligopeptide consisting essentially of D-amino acids and having an amino acid sequence selected from:

D-|Arg—Lys—Lys—Arg—Arg—Gln—Arg—Arg—Arg|;

D-|Arg—Arg—Arg—Arg—Arg—Arg—Arg—Arg—Arg|; and

D-|Arg—Arg—Arg—Gln—Arg—Arg—Arg—Arg—Arg|.

As noted hereinabove, the compounds of the present invention are desirably those of formula (Ib)

Np—|X|—Cp  (Ib)

wherein X represents an oliogopeptide as defined above, Np represents an N-terminal protecting group, and Cp represents a carboxyl terminal protecting group. Any chemical group which serves to protect peptide ends from undesired chemical attack can be used. Carboxyl terminal protecting groups and N-terminal protecting groups employed conventionally in the art of peptide synthesis are most desirably incorporated in the compounds of the present invention. Useful N-terminal protecting groups include, for example, loweralkanoyl groups of the formula R—C(O)— wherein R is a linear or branched lower alkyl chain comprising from, 1–5 carbon atoms. A preferred N-terminal protecting group is acetyl, $C_3C(O)$—. Also useful as N-terminal protecting groups are amino acid analogues lacking the amino function.

Preferred C-terminal protecting groups are, similarly, those used conventionally in the art of peptide synthesis. Such C-terminal protection may be achieved by incorporating the blocking group via the carbon atom of the carboxylic function, for example to form a ketone or an amide, or via the oxygen atom thereof to form an ester. Thus, useful carboxyl terminal protecting groups include, for example, ester-forming alkyl groups, particularly lower alkyl groups such as e.g., methyl, ethyl and propyl, as well as amide-forming amino functions such as primary amine (—NR2), as well as monoalkylamino and dialkylamino groups such as methylamino, ethylamino, dimethylamino, diethylamino, methylethylamino and the like. C-terminal protection can also be achieved by incorporating as the C-terminal amino acid a decarboxylated amino acid analogue, such as agmatine. Of course, N- and C-protecting groups of even greater structural complexity may alternatively be incorporated, if desired.

Especially preferred compounds of the invention, which conform to formula (Ib), are acetyl-[(D-Arg)$_9$]—NH$_2$; acetyl-(D-Arg)$_3$—(D-Gln)—(D-Arg)$_5$—NH$_2$; and acetyl-[D-(Arg—Lys—Lys—Arg—Arg—Gln—Arg—Arg—Arg)]—NH$_2$.

It will be appreciated that the oligopeptide may be conjugated, either through its C-terminus or its N-terminus to other amino acids without necessarily sacrificing the characteristic transactivation-deficiency and Tar-binding property exhibited by the oligopeptide, as determined by the assays herein described. The present invention thus further embraces Tar-binding, transactivation deficient polypeptide compounds which incorporate the oligopeptides described herein and conform to the general formula, I.e.

R1—(A)m—[X]—(B)n—R2  (I)

wherein at least one of m and n is 1, A and B independently represent one or more amide-linked, alpha amino acids, and R1, R2 and X are as specified above. Desirably, R1 represents an N-terminal protecting group, Np, and R2 represents a carboxyl terminal protecting group, Cp, wherein Np and Cp are as defined above.

Specifically contemplated compounds of formula I are transactivation-deficient fragments and variants of HIV tat in which the resident basic domain (residues 49–57) is replaced by an oligopeptide of the present invention. It has been shown, for example, that variants of tat (37–62) in which alanine substitutions are introduced at positions flanking the basic domain e.g. positions 41, 46 and/or 47 exhibit strong antagonist activity (Green et al, supra). Specifically contemplated are compounds in which the basic domain of such tat (37–62)-based antagonists is replaced by an oligopeptide of the present invention. Most desirably, amino acids representing A and B in the above formula I are D-amino acids.

The compounds of the present invention can be readily prepared by standard, well-established solid-phase peptide synthesis methods (SPPS), general descriptions of which appear, for example, in J. M. Stewart and J. D. Young, *Solid Phase Peptide Synthesis*, 2nd Edition, 1984, Pierce Chemical Company, Rockford, Ill.; and in M. Bodanszky and A. Bodanaszky, *The Practice of Peptide Synthesis*, 1984, Springer-Verlag, New York; Applied Biosystems 430A Users Manual, 1987, ABI Inc., Foster City, Calif.

In general, a suitably protected amino acid is attached through its carboxyl group (—COOH) to a derivatized, insoluble polymeric support, e.g. cross-linked polystyrene or polyamide resin. "Suitably protected" refers to the presence of protecting groups on the alpha-amino group (α-$NH_2$) and side-chain functional group (if present) of the amino acid. Synthesis proceeds in a stepwise, cyclical fashion by successively removing the α-$NH_2$ protecting group, then coupling an activated amino acid to the newly freed α-$NH_2$. Activation of the —COOH group of the incoming amino acid can be effected directly via a carbodiimide, e.g. dicyclohexylcarbodiimide (DCC) or diisopropylcarbodiimide (DIC), via formation of the symetric acid anhydride, or preferably by formation of an "active ester", e.g. hydroxybenzotriazole (HOBt), pentafluorophenyl, para-nitrophenyl or N-hydroxysuccinimide esters. Suitable side-chain protecting groups generally are stable to all of the reagents, solvents and reaction conditions used during synthesis, yet removable under conditions which will not affect the integrity of the final peptide product.

The two preferred methods of solid phase peptide synthesis are the BOC and FMOC methods, so called for their use of the tert-butyloxycarbonyl and 9-fluorenylmethyloxycarbonyl groups, respectively, to protect the α-$NH_2$ of the amino acid residues.

In the more established BOC method, the acid-lability of the BOC group is exploited and trifluoracetic acid (TFA) treatment is used to effect its removal. The preferred amino acid side-chain protecting groups (for examples see Table 1 below) are relatively stable in weak acid, e.g. TFA. Most can be cleaved by very strong acids such as hydrofluoric (HF) or trifluoromothanesulfonic acid (TFMSA). A few side-chain protecting groups, e.g. His(Dnp) & Met(O), may require a separate deprotection step, e.g. thiophenol or ammonolysis, mercaptopyridine or mercaptoethanol treatment, respectively. After synthesis, the peptide is typically cleaved from the resin and simultaneously deprotected by HF treatment at low temperature, e.g. 0° C.

TABLE 1

Examples of Side-Chain Protecting Groups Used in SPPS by the BOC Method

| Residue | Side-Chain Moiety | Protecting Group |
|---|---|---|
| Arginine | guanidino | p-toluenesulfonyl (Tos); methoxybenzenesulfonyl (Mts); nitro. |
| Aspartic Acid, Glutamic Acid | carboxyl | ortho-benzyl (OBzl) |
| Cysteine | sulfhydryl/thiol | p-methylbenzyl (CH$_3$Bzl) |
| Histidine | imidazole N—H | 2,4-dinitrophenyl (Dnp); (Tos) |
| Lysine | amino | 2-chlorobenzyloxycarbonyl (Cl—Z) |
| Methionine | sulfide/thioester | sulfoxide (O); none |
| Serine, Threonine | hydroxy | benzayl (Bzl) |
| Tryptophan | indole N—H | formyl (CHO) |
| Tyrosine | hydroxy | 2-bromobenzyloxycarbonyl (Br—Z) |

In the more recently developed FMOC method the base labile FMOC group is removed using a mild organic base, e.g. piperidine, thereby allowing the use of side-chain protecting groups which are labile to milder acid treatment, e.g. TFA (for examples see Table 2). An acid labile ether resin such as HMP-resin (para-hydroxymethylphenoxymethyl polystyrene) is used as the solid support, permitting simultaneous cleavage/deprotection in TFA.

TABLE 2

Examples of Side-Chain Protecting Groups Used in SPPS by the FMOC Method

| Residue | Side Chain Moiety | Protecting Group |
|---|---|---|
| Arginine | guanidino | 4-methoxy-2,3,6-trimethyl-benzenesulfonyl (Mtr); pentamethylchroman-6-sulfonyl |
| Aspartic Acid, Glutamic Acid | carboxyl | t-butyl ester (OtBu) |
| Cysteine | sulfhydryl/thiol | trityl (Trt); acetamidomethyl (Acm) |
| Histidine | imidazole N—H | Trt |
| Lysine | amino | t-butyloxycarbonyl (BOC) |
| Serine, Threonine, Tyrosine | hydroxyl | t-butyl (tBu) |

Suitably protected and/or preactivated D- and/or L-amino acids, derivatized and/or preloaded resins, and all ancillary reagents and solvents required for either BOC or FMOC peptide synthesis are commercially available from several suppliers. In addition, automated peptide synthesizers with optimized, pre-programmed BOC and/or FMOC synthesis cycles are available from numerous commercial sources.

Incorporation of N- and/or C- protecting groups can also be achieved using protocols conventional to solid phase peptide synthesis methods. For incorporation of C-terminal protecting groups, for example, synthesis of the desired peptide is typically performed using, as solid phase, a supporting resin that has been chemically modified so that cleavage from the resin results in a peptide having the desired C-terminal protecting group. To provide peptides in which the C-terminus bears a primary amino protecting group, for instance, synthesis is performed using a p-methylbenzhydrylamine (MBHA) resin so that, when peptide synthesis is completed, treatment with hydrofluoric acid releases the desired C-terminally amidated peptide.

Similarly, incorporation of an N-methylamine protecting group at the C-terminus is achieved using N-methylaminoethyl-derivatized DVB resin, which upon HF treatment releases peptide bearing an N-methylamidated C-terminus. Protection of the C-terminus by esterification can also be achieved using conventional procedures. This entails use of resin/blocking group combination that permits release of side-chain protected peptide from the resin, to allow for subsequent reaction with the desired alcohol, to form the ester function. FMOC protecting groups, in combination with DVB resin derivatized with methoxyalkoxy-benzyl alcohol or equivalent linker, can be used for this purpose, with cleavage from the support being effected by TFA in dicholoromethane. Esterification of the suitably activated carboxyl function e.g. with DCC, can then proceed by addition of the desired alcohol, followed by deprotection and isolation of the esterified peptide product.

Incorporation of N-terminal protecting groups can be achieved while the synthesized peptide is still attached to the resin, for instance by treatment with suitable anhydride and nitrile. To incorporate an acetyl protecting group at the N-terminus, for instance, the resin-coupled peptide can be treated with 20% acetic anhydride in acetonitrile. The N-protected peptide product can then be cleaved from the resin, deprotected and subsequently isolated.

Once the desired peptide sequence has been synthesized, cleaved from the resin and fully deprotected, the peptide is then purified to ensure the recovery of a single oligopeptide having the selected amino acid sequence. Purification can be achieved using any of the standard approaches, which include reversed-phase high-pressure liquid chromatography (RP-HPLC) on alkylated silica columns, e.g. $C_4$-, $C_8$-, or $C_{18}$- silica. Such column fractionation is generally accomplished by running linear gradients, e.g. 0–50%, of increasing % organic solvent, e.g. acetonitrile, in aqueous buffer, usually containing a small amount of TFA, e.g. 0.1%. Alternatively, ion-exchange HPLC can be employed to separate peptide species on the basis of their charge characteristics. Column fractions are collected, and those containing peptide of the desired/required purity are pooled together. The peptide is typically then treated to exchange the cleavage acid (e.g. TFA) with a pharmaceutically acceptable acid, such as acetic acid, to provide a water soluble salt of the peptide.

Following purification, it is desirable to analyze the oligopeptide further to ensure its chemical authenticity. This is most conveniently achieved through amino acid composition analysis. To analyze amino acid composition, a sample of purified oligopeptide is completely hydrolysed in aqueous acid, e.g. HCl, and the resulting mixture of amino acids separated, identified and quantitated via HPLC, e.g. Waters Pico-Tag system, or automated analyzer, e.g. Beckman 6300 Amino Acid Analyzer. A more definitive measure of authenticity is full sequence analysis of the peptide. Several protein sequenators which sequentially degrade the peptide and identity the linear order of its amino acids are used for this purpose, and are available from several commercial sources. High-resolution mass spectrometry methods can also be applied, to generate exact molecular weight information.

For therapeutic use, the oligopeptide compounds of the invention are desirably of "pharmaceutical grade" purity, a term used herein with reference to an oligopeptide preparation which has been shown to migrate as a single peak on HPLC, to exhibit uniform and authentic amino acid composition and sequence upon analysis thereof, and which otherwise meets standards set by the various national bodies which regulate quality of pharmaceutical products.

For therapeutic use, compounds of the present invention exhibiting pharmaceutical grade purity are combined with pharmaceutically acceptable carriers to generate compositions suitable for administration to patients. Any of the carriers conventionally used in the pharmaceutical industry may be employed, such as diluents, excipients and the like. According to a preferred embodiment of the invention, the compounds are formulated for administration by injection, either sub-cutaneously or intravenously, and are accordingly provided as aqueous, buffered compositions, in sterile and pyrogen-free form. The compounds herein designated as preferred compounds are substantially water-soluble. Water solubility of these and other compounds of the invention may be enhanced, if desired, by incorporating a solubility enhancer, such as cetyltrimethylammonium bromide or chloride. Alternatively, the compounds of the present invention may be formulated for administration by routes other than injection, of course. Compositions for topical application, such as creams, lotions or ointments can be used, as may aerosol inhalable formulations. Oral dosage forms, such as tablets, capsules and the like, formulated in accordance with standard pharmaceutical practise, may also be employed.

Pharmaceutical compositions containing a compound of the present invention are useful to treat HIV-infected patients, i.e. patients diagnosed as being carriers of the HIV virus. The compounds of the invention are most desirably administered to HIV-infected patients before clinical symptoms of the AIDS syndrome are manifest, as a means of delaying and/or arresting progression of the syndrome. Suitable treatment regimens are those which maintain in the patient a serum level of the compound sufficient to control HIV replication. The establishment in the patient of such effective levels will be reflected, in appropriately controlled trials, by a reduction in the rate at which T4 lymphocytes are depleted, or by the absence in patient plasma samples of an increase in HIV antigens, such as p24.

It is anticipated that an effective treatment regimen will entail intravenous administration of dosages sizes in the range from 1 ug to about 10 mg per kg, and such as between about 10 ug/kg to about 5 mg/kg. For example, it is anticipated that the peptide designated herein as peptide 4C i.e. acetyl-[D-Arg$_9$]—NH$_2$, will be effective when present in serum at a concentration between about 1 uM and 100 uM, and that this serum concentration can be achieved through maintenance doses in the size range from about 0.1 mg/kg to about 5 mg/kg. It will be appreciated however, that affective dosage sizes will vary according to the route of administration, and the frequency of administration. For example, smaller doses may suffice if administered on a daily basis, and larger doses may be required if administration frequency is extended, or if the compound is administered by a route other than intravenous injection.

EXAMPLES

To evaluate the effect of amino acid substitution in the tat basic domain on TAR-binding affinity and specificity, oligopeptide variants thereof were synthesized using the solid phase synthesis approach, and then purified to homogeneity as measured by various means including high performance liquid chromatography (HPLC). Amino acid composition analysis was employed to confirm authenticity of all oligopeptides, except the arginine homopolymer the chemical authenticity of which was confirmed by fast atom bombardment mass spectroscopy.

TAR-binding affinity of the oligopeptides relative to HIV tat(1–86) and relative to tat fragments representing the tat basic domain, was evaluated by RNA gel mobility shift assay using as ligand a truncated functional form of TAR RNA having the sequence (SEQ ID NO:13) shown below. For comparison, the binding affinity for a variant of TAR (SEQ ID NO:14) which does not bind tat, was also assayed in the same manner, to evaluate the specificity for TAR.

Synthesis of the TAR fragment and its variant analogue was accomplished as described by Roy et al. in Genes and Development, 1990, 4:1365. The TAR-binding assay was also performed in the manner reported by Roy et al. supra, which is incorporated herein by reference.

Example 1

Effect of glutamine substitution on TAR-binding affinity

To assess the contribution to TAR-binding of the glutamine residue internal to the tat basic domain, a series of glutamine-substituted analogues was synthesized and then assayed in the RNA gel mobility shift assay for TAR-binding activity.

Each of the oligopeptides was synthesized by, and purchased from, the American Peptide Company, using the solid phase peptide synthesis approach, and in accordance with protocols conventional thereto. More particularly, synthesis was performed on a Beckman 990 synthesizer, using chloromethyl-polystyrene as solid support, and Boc-based protocols and protecting groups, to generate the following compounds;

1A) (SEQ ID NO:4 wherein Xaa is Gly) $^{47}$Tyr—Gly—Arg—Lys—Lys—Arg—Arg—Gly—Arg—Arg—Arg—Pro$^{60}$ 1B) (SEQ ID NO:4 wherein Xaa is Cys) Tyr—Gly—Arg—Lys—Lys—Arg—Arg—Cys—Arg—Arg—Arg—Pro 1C) (SEQ ID NO:4 wherein Xaa is His) Tyr—Gly—Arg—Lys—Lys—Arg—Arg—Ser—Arg—Arg—Arg—Pro 1D) (SEQ ID NO:4 wherein Xaa is His) Tyr—Gly—Arg—Lys—Lys—Arg—Arg—His—Arg—Arg—Arg—Pro 1E) (SEQ ID NO:4 wherein Xaa is Lys) Tyr—Gly—Arg—Lys—Lys—Arg—Arg—Lys—Arg—Arg—Arg—Pro 1F) (SEQ ID NO:4 wherein Xaa is Asn) Tyr—Gly—Arg—Lys—Lys—Arg—Arg—Asn—Arg—Arg—Arg—Pro 1G) (SEQ ID NO:4 wherein Xaa is homoGlyn) Tyr—Gly—Arg—Lys—Lys—Arg—Arg—homoGln—Arg—Arg—Arg—Pro The TAR-binding affinity was then evaluated in the RNA gel mobility shift assay described hereinabove, and compared with tat (1-86) and the corresponding wild type oligopeptide. Results indicated that substitution of glutamine by glycine and cysteine reduced TAR-binding affinity whereas oligopeptides in which glutamine was replaced by serine, histidine, asparagine or homoglutamine each displayed an affinity for TAR similar to tat (1-86) and an oligopeptide representing the basic domain thereof. Surprisingly, however, substitution of glutamine by lysine resulted in an oligopeptide which displayed far greater affinity for binding with TAR.

Example 2

Evaluation of the positional significance of Gln$^{54}$

To investigate the positional significance of the glutamine residue in the tat basic domain, a series of analogues was designed in which the position of the glutamine varied in the context of an otherwise homopolymeric L-arginine non-amer. Oligopeptides in this series were also purchased from American Peptide Company, and were synthesized by BOC chemistry and purified using conventional procedures, to yield the acetate salt of the following compounds:

2A) (SEQ ID NO:5) Arg—Gln—Arg—Arg—Arg—Arg—Arg—Arg—Arg 2A.5) (SEQ ID NO:6) Arg—Arg—Gln—Arg—Arg—Arg—Arg—Arg—Arg 2B) (SEQ ID NO:7) Arg—Arg—Arg—Gln—Arg—Arg—Arg—Arg—Arg 2B.5) (SEQ ID NO:8) Arg—Arg—Arg—Arg—Gln—Arg—Arg—Arg—Arg

2C) SEQ ID NO:9) Arg—Arg—Arg—Arg—Arg—Gln—Arg—Arg—Arg

2D) SEQ ID NO:11) Arg—Arg—Arg—Arg—Arg—Arg—Arg—Gln—Arg

TAR RNA binding assays revealed that each oligopeptide in this series bound TAR with affinity comparable to both tat (1-86) and the oligopeptide representing its basic domain. Each oligopeptide further displayed a specificity for binding to the functional TAR fragment as determined by the absence of substantial binding to the TAR variant.

Example 3

Synthesis of L-(Arg—Arg—Arg—Arg—Arg—Arg—Arg—Arg—Arg) (amino acid residues 1-9 of SEQ ID NO:12)

With the results of examples 1 and 2 suggesting that the internal glutamine residue can be sacrificed, synthesis and evaluation of an L-Arg nonamer were undertaken. Nona-L-arginine, (L-Arg), was prepared by the BOC solid-phase synthesis method. Synthesis was performed by The American Peptide Company using a Beckman 990 synthesizer and chloromethylpolystyrene resin as solid support.

The tert-butyloxycarbonyl group (BOC) was used to protect the $\alpha$-NH$_2$ function of L-arginine during the synthesis. The guanidino function was protected with the para-toluenesulfonyl group (Tos). Couplings were carried out using excess hydroxybenzotriazole (HOBt)-activated ester of BOC-L-Arg(Tos). Removal of the BOC protecting group after each cycle was effected with TFA. The final peptide, (L-Arg)$_9$ was cleaved from the polymer resin and the Tos protecting groups removed via standard HF treatment. After removal of HF, the peptide+resin mixture was washed with diethyl ether and extracted with aqueous acetic acid.

The crude peptide was lyophilized, then fractionated by RP-HPLC on a C$_{18}$ silica column using a gradient of 2-40% acetonitrile in 0.1% TFA. Fractions were collected and checked by analytical RP-HPLC. Those containing ≧95% of the major product were combined. High resolution mass spectrometry showed the product to be the expected L-(Arg)$_9$.

The TAR binding studies revealed that the arginine homopolymer bound with greater affinity to TAR RNA than either tat (1-86), the oligopeptide representing the basic domain thereof, or any one of the oligopeptide analogues described in examples 1 and 2. The arginine homopolymer also bound selectively to the functional TAR fragment.

Example 4

Synthesis of D-(Arg—Lys—Lys—Arg—Arg—Gln—Arg—Arg—Arg)

The named D-peptide is readily prepared by the FMOC solid-phase synthesis method and an automated synthesizer, e.g. Applied Biosystems 430A.

$\alpha$-Amino groups of the D-amino acids are protected with the base-labile fluorenylmethyloxycarbonyl group (FMOC). The lysine and arginine side-chains are protected via acid-labile protecting, e.g. BOC an methoxytrimethylbenzenesulfonyl (MtR), respectively.

The C-terminal FMOC-D-Arg(Mtr) residue is double-coupled to a suitably derivatized polystyrene resin, e.g. HMP-polystyrene, via the symmetric anhydride. Removal of the FMOC group is carried out in 20% piperidine. Addition of amino acid residues to the peptide-resin is effected via their activated HOBt esters.

Cleavage and deprotection of the final peptide is carried out by treatment with TFA. The crude peptide is purified by RP-or ion exchange HPLC. The purified product is characterized by standard amino acid analysis and/or mass spectrometry and/or sequence analysis.

A purified form of the named D-oligopeptide synthesized as described above was purchased from a commercial source, and tested in the TAR RNA binding assay. The results of the assay revealed binding of the oligopeptide to the RNA, indicating that Tar binding is retained by oligopeptides in which L-amino acids are replaced by the corresponding D-amino acids.

Example 5

Synthesis of acetyl-[D-Arg]$_9$—NH$_2$

The title compound, designated compound 4C, was synthesized using p-methylbenzhydrylamine (MBHA) resin as solid support, to provide the C-terminal blocking amine on the resultant peptide. Synthesis proceeded using D-arginine residues in which the amino function was blocked with the t-BOC group, and the guanidino function was blocked with the Tos group. Coupling cycles and deprotection were performed as described for the L-Arg nonamer (Example 3). When coupling cycles were completed, the resin-bound paptide was treated with 20% acetic anhydride in acetonitrile, to incorporate an acetyl protecting group at the N-terminus thereof. Liberation of peptide from the resin, and removal of Tos groups, were achieved by treatment with hydrofluoric acid, yielding the C-terminally amidated, title compound. After removal of hydrofluoric acid, the resin/peptide mixture was washed with diethyl ether and extracted with aqueous acetic acid. The crude peptide was lyophilized, and then purified by RP-HPLC fractionation as described in Example 3. High resolution mass spectrometry showed the product to the desired compound.

TAR-binding studies, performed using the mobility shift assay, indicated that the N- and C-protected D-Arg nonamer exhibits a TAR-binding affinity comparable to the basic domain of wild type tat. Binding studies have further revealed that this compound binds to the functional Tar molecule with specificity comparable to the wild type basic domain, relative to binding with the non-functional TAR variant. The specificity of binding has also been confirmed in studies comparing TAR binding with yeast tRNA binding.

Example 6

Using synthesis protocols described in Example 5, to incorporate an amidated C-terminus and an acetylated N-terminus, the following additional oligopeptides consisting essentially of D-amino acids were synthesized and purified for testing in the HIV inhibition assay:

4G: acetyl-|D-(Arg—Lys—Lys—Arg—Arg—Gln—Arg—Arg—Arg)]—NH$_2$;

4H: acetyl-(D-Arg)$_3$—(D-Gln)—(D-Arg)$_5$—NH$_2$;

4J: acetyl-|D-(Arg)$_8$]—NH$_2$;

4K: acetyl-[D-(Arg)$_7$]—NH$_2$.

Example 7

Inhibition of HIV replication

Selected compounds of the present invention were tested for the ability to inhibit HIV replication in virally infected cells of the HuT78 lineage (a human cutaneous T cell lymphoma line, available from ATCC under accession number ATCC TIE 161). Briefly, Hut78 cells (1×10$^6$) were maintained for a period of either 7 days or 14 days in growth medium containing selected oligopeptide at a concentration of 5 uM. At the end of the maintenance period, the cells were washed 3 times in growth medium and placed in triplicate T-25 flasks at a concentration of 2×10$^6$ cells in 5 ml of growth medium. Cells were then infected with HIV (strain NL4-3) using an inoculum of 0.1 virions/cell. After an incubation period of two hours, with mixing every 30 minutes, the virus inoculum was removed and replaced with growth medium. Four hours later, the selected oligopeptide was added to the growth medium, to a final concentration of 10 uM. At four and seven days after infection, samples of culture medium were removed and tested for the presence of p24 antigen, using an ELISA-based immunoassay kit available from Coulter Immunology (Hialeah, Fla., USA), in the manner instructed by the supplier. The cultures were also monitored for HIV-induced cytopathic effects. Controls used water in place of peptide.

Figure 1:
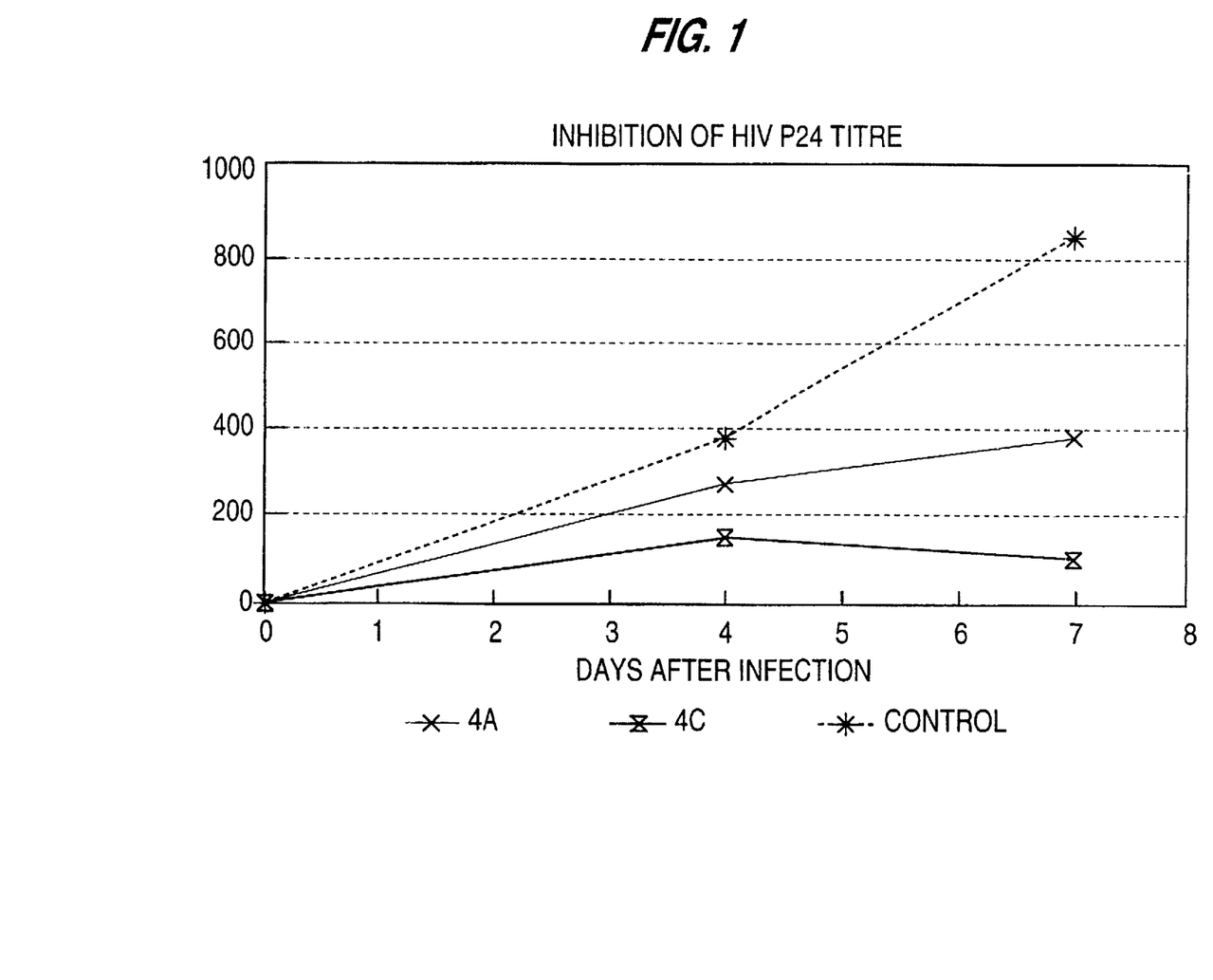
FIG. 1 illustrates graphically the results of HIV inhibition with compounds of the present invention.

Results of the assay, performed with oligopeptide 4A (D-|Arg—Lys—Lys—Arg—Arg—Gln—Arg—Arg—Arg|, example 4) and with oligopeptide 4C (the D-Arg nonamer with protected ends, example 5) are graphed in FIG. 1 (experiment 1 results). Results with these peptides, and with similarly assayed peptide 4G, i.e., acetyl-|D-(Arg—Lys—Lys—Arg—Arg—Gln—Arg—Arg—Arg|—NR$_2$ (example 6) are also tabulated below:

| Days After Infection | P$_H$ Titers pg/ml | | | | | |
|---|---|---|---|---|---|---|
| | 24 Hrs Pretreatment | | 7 Day Pretreatment | | 14 Day Pretreatment | |
| | Day 4 | Day 7 | Day 4 | Day 7 | Day 4 | Day 7 |
| Peptide Expt 1 | | | | | | |
| 4A1 | | | 266.3 | 376.4 | 484.8 | 3049 |
| 4A2 | | | 277.7 | 376.5 | 459.9 | 2662 |
| 4C1 | | | 168.4 | 100.76 | 152.5 | 175.1 |
| 4C2 | | | 131.5 | 100.72 | 129.0 | 133.6 |
| Control 1 | | | 356.5 | 892.4 | 690.0 | 3829 |
| Control 2 | | | 395.5 | 801.0 | 658.0 | 3239 |
| Expt 2 | | | | | | |
| 4C1 | | | 98.08 | 48.33 | | |
| 4C2 | | | 93.76 | 43.24 | | |
| Control 1 | | | 446.50 | 4187.0 | | |
| Control 2 | | | 404.10 | 3173.8 | | |
| Expt 3 | | | | | | |
| 4G1 | 340.9 | 721.1 | 312.1 | 371.5 | | |
| 4G2 | 356.9 | 851.8 | 336.1 | 446.8 | | |
| Control 1 | 473.7 | 1,452.8 | 372.1 | 1,348.4 | | |
| Control 2 | 559.2 | 1,561.3 | 296.9 | 1,652.7 | | |

The results show that incubation of the cells with a 5 uM concentration of selected oligopeptide induces significant resistance to viral infection. At the concentration tested, peptide 4C achieves a 95% or better inhibition of viral replication, as measured by p24 assay (FIG. 1). Visual inspection of the cells demonstrated that all selected peptides completely inhibited the formation of syncytia, a characteristic of HIV-infected cells in culture. There was no apparent inhibition of host cell replication at this concentration when peptide 4C was tested. In separate experiments, a 100 uM concentration of peptide 4C was found to have no significant detrimental effect on cell replication, although some reduction was noted at 500 uM. This indicates that 4C can be formulated and used at therapeutic, non-toxic doses.

As will be seen from the above Table, peptides 4A and 4G also exhibited positive effects on HIV inhibition at 5 uM concentrations, particularly following pretreatment for the shorter, 7 day period.

---

We claim:

1. A compound of the formula wherein

R1 is H or a conventional amino protecting group;

R2 is OH or a conventional carboxyl protecting group;

X is a TAR-binding, transactivation-deficient oligopeptide analog of the HIV tat basic domain consisting of 6–11 basic amino acids and one amino acid other than a basic amino acid, and wherein each amino acid is independently D or L.

2. A compound according to claim 1 wherein the non-basic amino acid is glutamine.

3. A compound according to claim 1 wherein X is an oligopeptide comprising 6–10 arginines and one glutamine.

4. A compound according to claim 1, wherein X represents an oligopeptide consisting essentially of D-amino acids.

5. A compound of the formula wherein

R1 is H;

R2 is OH;

X is a TAR-binding, transactivation-deficient oligopeptide analog of the HIV tat basic domain consisting of 7–12 basic amino acids, with the proviso that at least one of the amino acids is of the D-configuration, and with the further proviso that at least one of the amino acids is other than lysine.

6. A compound according to claim 5, wherein X represents an oligopeptide consisting essentially of D-amino acids.

7. A compound of the formula wherein

R1 is H or a conventional amino protecting group;

R2 is OH or a conventional carboxyl protecting group;

X is a TAR-binding, transactivation-deficient oligopeptide analog of the HIV tat basic domain consisting of 7–12 basic amino acids, and wherein each amino acid is independently D or L;

with the proviso that, in said compound, R1 is not H when R2 is OH.

8. A compound according to claim 7, wherein X represents an oligopeptide consisting essentially of D-amino acids.

9. A compound according to claim 7, wherein X is —(D-Arg)$_9$—.

10. A compound of the formula wherein

R1 is selected from the group consisting of hydrogen, lower alkanoyl, and a deaminated amino acid;

R2 is selected from the group consisting of OH, lower alkyl, amino, N-(loweralkyl)amino, N,N-di-(loweralkyl)amino and a decarboxylated amino acid;

X is a TAR-binding, transactivation-deficient oligopeptide analog of the HIV tat basic domain consisting of 7–12 basic amino acids, and wherein each amino acid is independently D or L;

with the proviso that, in said compound, R1 is not H when R2 is OH.

11. A compound according to claim 10, wherein X represents an oligopeptide consisting essentially of D-amino acids.

12. A compound according to claim 10, wherein X is —(D-Arg)$_9$—.

13. A compound of the formula wherein

R1 is selected from the group consisting of hydrogen, lower alkanoyl, and a deaminated amino acid;

R2 is selected from the group consisting of OH, lower alkyl, amino, N-(loweralkyl)amino, N,N-di-(loweralkyl)amino and a decarboxylated amino acid;

X is a TAR-binding, transactivation-deficient oligopeptide analog of the HIV tat basic domain consisting of 6–11 basic amino acids and one amino acid other than a basic amino acid, and wherein each amino acid is independently D or L;

with the proviso that in said compound, if R1 is hydrogen and concommitantly R2 is amino, the non-basic amino acid present in X is other than glutamine, asparagine, and homoglutamine.

14. A compound according to claim 13, wherein X represents an oligopeptide consisting essentially of D-amino acids.

15. A compound of the formula wherein

R1 is selected from the group consisting of hydrogen, a conventional amino protecting group, a lower alkanoyl group, and a deaminated amino acid;

R2 is selected from the group consisting of OH, a conventional carboxyl protecting group, a lower alkyl group, an amino group, a N-(loweralkyl)amino group, an N,N-di-(loweralkyl)amino group and a decarboxylated amino acid;

X is a TAR-binding, transactivation-deficient oligopeptide analog of the HIV tat basic domain selected selected from the group consisting of:

Arg—Lys—Lys—Arg—Arg—Asn—Arg—Arg—Arg (SEQ ID NO:2 wherein Xaa is Asn);

Arg—Lys—Lys—Arg—Arg—homoGln—Arg—Arg—Arg (SEQ ID NO:2 wherein Xaa is homoGln); and

Arg—Arg—Arg—Arg—Arg—Gln—Arg—Arg—Arg (SEQ ID NO:9);

wherein in said oligopeptide, each amino acid is independently either D or L;

with the proviso that if R is an amino group, R1 is not hydrogen.

16. A compound according to claim 15, wherein X represents an oligopeptide consisting essentially of D-amino acids.

17. A compound of the formula wherein

R1 is selected from the group consisting of hydrogen, a conventional amino protecting group, a lower alkanoyl group, and a deaminated amino acid;

R2 is selected from the group consisting of OH, a conventional carboxyl protecting group, a lower alkyl group, an amino group, a N-(loweralkyl)amino group, an N,N-di-(loweralkyl)amino group and a decarboxylated amino acid;

X is a TAR-binding, transactivation-deficient oligopeptide analog of the HIV tat basic domain selected selected from the group consisting of:

Arg—Lys—Lys—Arg—Arg—Ser—Arg—Arg—Arg (SEQ ID NO:2 wherein Xaa is Ser);

Arg—Gln—Arg—Arg—Arg—Arg—Arg—Arg—Arg (SEQ ID NO:5);

Arg—Arg—Gln—Arg—Arg—Arg—Arg—Arg—Arg (SEQ ID NO:6);

Arg—Arg—Arg—Gln—Arg—Arg—Arg—Arg—Arg (SEQ ID NO:7);

Arg—Arg—Arg—Arg—Gln—Arg—Arg—Arg—Arg (SEQ ID NO:8);

Arg—Arg—Arg—Arg—Arg—Arg—Gln—Arg—Arg (SEQ ID NO:10);

Arg—Arg—Arg—Arg—Arg—Arg—Arg—Gln—Arg (SEQ ID NO:11);

wherein in said oligopeptide, each amino acid is independently either D or L.

18. A compound according to claim 17, wherein X represents an oligopeptide consisting essentially of D-amino acids.

19. A compound of the formula

R1—X—R2 wherein

R1 is selected from the group consisting of hydrogen, a conventional amino protecting group, a lower alkanoyl group, and a deaminated amino acid;

R2 is selected from the group consisting of OH, a conventional carboxyl protecting group, a lower alkyl group, an amino group, a N-(loweralkyl)amino group, an N,N-di-(loweralkyl)amino group and a decarboxylated amino acid;

X is a TAR-binding, transactivation-deficient oligopeptide analog of the HIV tat basic domain selected selected from the group consisting of:

Arg—Lys—Lys—Arg—Arg—Lys—Arg—Arg—Arg (SEQ ID NO:2, wherein Xaa=Lys);

Arg—Lys—Lys—Arg—Arg—His—Arg—Arg—Arg (SEQ ID NO:2, wherein Xaa=His);

Arg—Lys—Lys—Arg—Arg—Arg—Arg—Arg—Arg (SEQ ID NO:3, wherein Xaa at position 2=Lys, Xaa at position 3=Lys, and Xaa at position 6=Arg);

Arg—Lys—Arg—Arg—Arg—Arg—Arg—Arg—Arg (SEQ ID NO:3, wherein Xaa at position 2=Lys, Xaa at position 3=Arg, and Xaa at position 6=Arg);

Arg—Arg—Lys—Arg—Arg—Arg—Arg—Arg—Arg (SEQ ID NO:3, wherein Xaa at position 2=Arg, Xaa at position 3=Lys, and Xaa at position 6=Arg);

Arg—Arg—Lys—Arg—Arg—Lys—Arg—Arg—Arg (SEQ ID NO:3, wherein Xaa at position 2=Arg, Xaa at position 3=Lys, and Xaa at position 6=Lys);

Arg—Arg—Arg—Arg—Arg—Lys—Arg—Arg—Arg (SEQ ID NO:3, wherein Xaa at position 2=Arg, Xaa at position 3=Arg, and Xaa at position 6=Lys);

Arg—Arg—Arg—Arg—Arg—Arg—Arg (amino acid residues 1–7 of SEQ ID NO:12);

Arg—Arg—Arg—Arg—Arg—Arg—Arg—Arg (amino acid residues 1–8 of SEQ ID NO:12);

Arg—Arg—Arg—Arg—Arg—Arg—Arg—Arg—Arg (amino acid residues 1–9 of SEQ ID NO:12);

Arg—Arg—Arg—Arg—Arg—Arg—Arg—Arg—Arg—Arg (amino acid residues 1–10 of SEQ ID NO:12);

Arg—Arg—Arg—Arg—Arg—Arg—Arg—Arg—Arg—Arg—Arg (amino acid residues 1–11 of SEQ ID NO:12); and Arg—Arg—Arg—Arg—Arg—Arg—Arg—Arg—Arg—Arg—Arg—Arg (SEQ ID NO:12).

wherein in said oligopeptide, each amino acid is independently either D or L;

with the proviso that, in said compound, if R1 is hydrogen and concommitantly R2 is OH, then at least one D-amino acid is present.

20. A compound according to claim 19, wherein X represents an oligopeptide consisting essentially of D-amino acids.

21. A compound selected from the group consisting of

D-(Arg—Lys—Lys—Arg—Arg—Gln—Arg—Arg—Arg—NH$_2$);

D-(Arg—Lys—Lys—Arg—Arg—homoGln—Arg—Arg—Arg—NH$_2$); and

D-(Arg—Lys—Lys—Arg—Arg—Asn—Arg—Arg—Arg—NH$_2$).

22. The compound acetyl-(D-Arg)$_9$—NH$_2$.

23. The compound D-(Arg—Lys—Lys—Arg—Arg—Gln—Arg—Arg—Arg).

24. The compound acetyl-[D-(Arg—Lys—Lys—Arg—Arg—Gln—Arg—Arg—Arg)—NH$_2$].

25. The compound acetyl-(D-Arg)$_3$-(D-Gln)—(D-Arg)$_5$—NH$_2$.

26. A pharmaceutical composition comprising a compound according to any of claims 1–25 together with a pharmaceutically acceptable carrier.

27. A method for treating an HIV infection in a patient, comprising administering to a patient infected with HIV a pharmaceutical composition according to claim 26.

28. The method according to claim 27, wherein X represents an oligopeptide consisting essentially of D-amino acids.

29. A method for treating an HIV infection in a patient, comprising administering to a patient infected with HIV a compound having the following structure:

R1—X—R2 wherein

R1 is H;

R2 is OH;

X is a TAR-binding, transactivation-deficient oligopeptide analog of the HIV tat basic domain consisting of 7–12 basic amino acids, each of which is independently of the D- or L-configuration.

30. The method according to claim 29, wherein X represents an oligopeptide consisting essentially of D-amino acids.

31. The method according to claim 27, wherein said pharmaceutical composition comprises a compound selected from the group consisting of acetyl-(D-Arg)$_3$—(D-Gln)—(D-Arg)$_5$—NH$_2$;

acetyl-(D-Arg)$_9$—NH$_2$; and acetyl-[D-(Arg—Lys—Lys—Arg—Arg—Gln—Arg—Arg—Arg)—NH$_2$].

* * * * *